United States Patent [19]

Brown

[11] 4,017,917
[45] Apr. 19, 1977

[54] COVER

[75] Inventor: Murray Hunter Brown, Santa Monica, Calif.

[73] Assignee: John R. Puckett, Pacific Palisades, Calif. ; a part interest

[22] Filed: Mar. 3, 1976

[21] Appl. No.: 663,367

[52] U.S. Cl. .................................. 5/60; 5/97; 5/284
[51] Int. Cl.² ................................ A47C 19/22
[58] Field of Search ............ 5/60, 92, 113, 97, 284, 5/362, 1 R, 1 B, 191 A, 192; 128/203, 204, 134

[56] References Cited

UNITED STATES PATENTS

| | | | |
|---|---|---|---|
| 2,917,753 | 12/1959 | Portis et al. | 5/60 |
| 3,100,900 | 8/1963 | Sidebotham | 5/284 |
| 3,316,565 | 5/1967 | Knowlton | 5/97 |
| 3,345,985 | 10/1967 | Fisher | 5/362 |
| 3,724,172 | 4/1973 | Wood | 128/191 A |

*Primary Examiner*—Casmir A. Nunberg
*Attorney, Agent, or Firm*—Forrest J. Lilly

[57] ABSTRACT

The application discloses a rigid or semi-rigid, two-part confining cover for a patient in a conventional hospital bed. The problem dealt with is that of a disturbed patient who would normally require confinement by ties, straps, or other conventional restraints, together with, in many cases, round-the-clock guarding by an attendant. The mattress support frame of a hospital bed usually has one or more horizontal pivot joints, the most important of which enables tilt-up of the back of the bed. Knee lift provisions are generally provided. The disclosed cover includes forward and rearward open-bottom shells, hinged to one another about the hinge axis of the bed used for tilt-up of the back part of the bed. The front shell has side walls rising from the longitudinal edges of the bed frame, forward of the aforementioned pivot axis, a front end closure, and a top closure. The back shell has side walls rising from the longitudinal edges of the bed frame from this pivot axis back, a rear end wall, and a top wall. The rear end of the front shell and the forward end of the rearward shell are fitted together in a manner to form a closure throughout the range of tilting of the rearward shell. The shells are perforated for air circulation, and are commodious enough to permit the patient adequate space for relatively free movement inside the closure. Access doors are provided.

1 Claim, 5 Drawing Figures

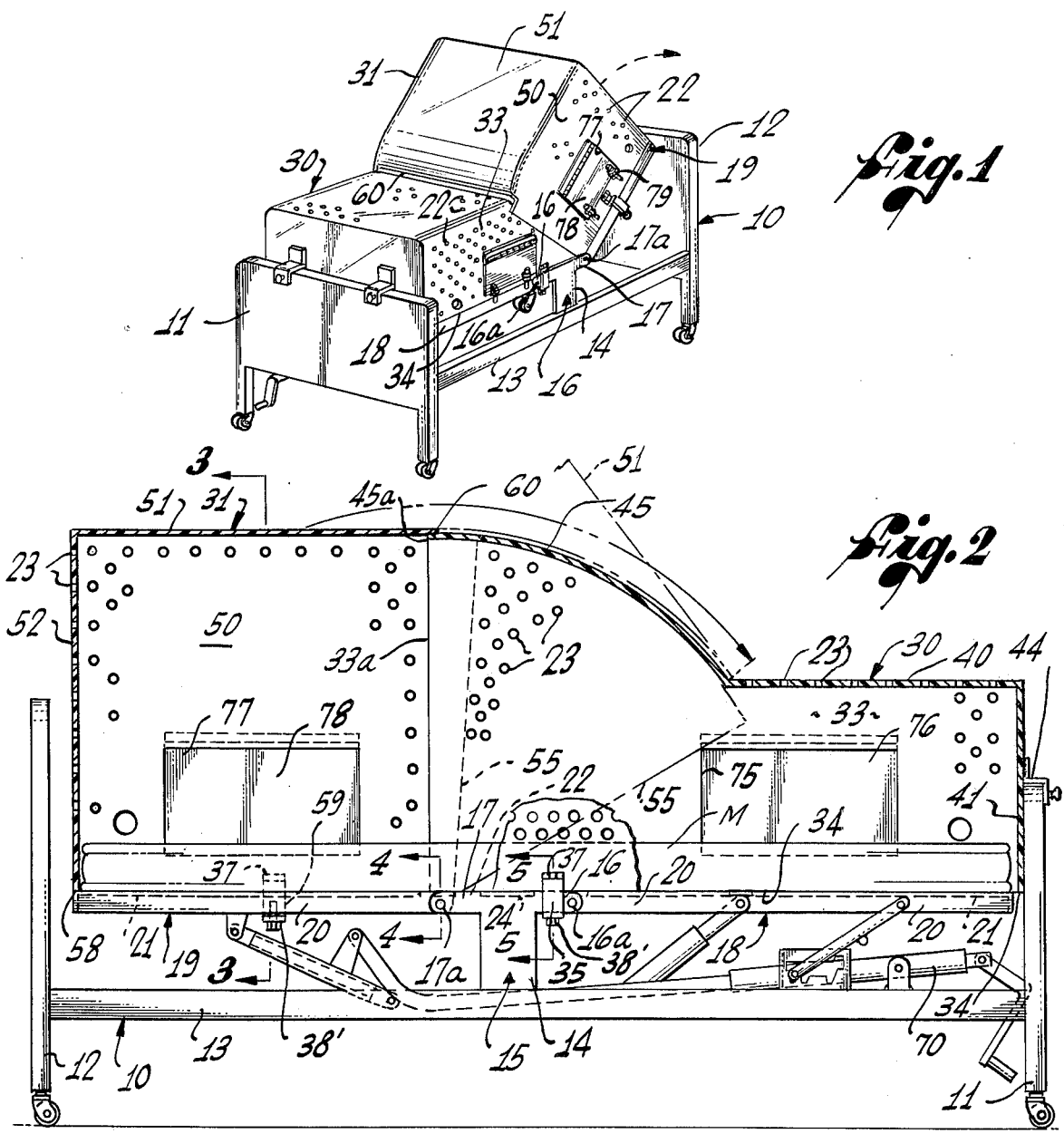
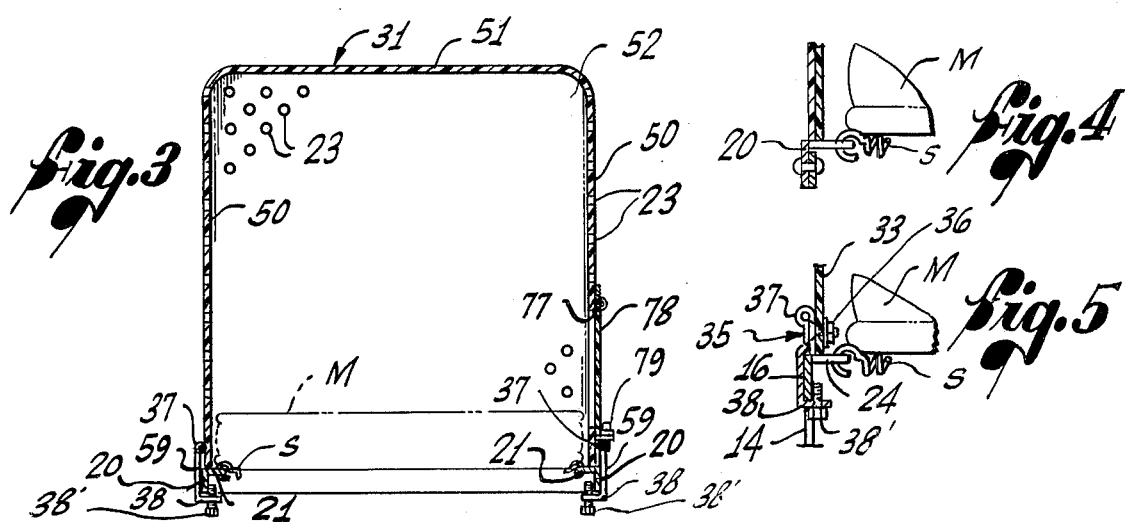

COVER

FIELD OF THE INVENTION

This invention relates generally to hospital bed facilities, and more particularly to a cover to afford protective security for confused, disturbed or hyperactive patients in their hospital beds.

BACKGROUND OF THE INVENTION

There is a longstanding problem in the secure bedding and confinement of certain classes of hospital patients who cannot be depended upon to lie properly in their beds, and there is often need for some much better form of restraint than is now known by which such patients can be kept safely in their beds. Restraints of the past and present run the gamut from side rails, arm and leg restraints, Posey belts, and often the full-time presence of nurses or attendants. A primary purpose of the invention is therefore the provision of an improved confining system designed to provide certain security for the confused, restless or disturbed patient, while allowing him a substantial degree of permissible freedom.

BRIEF SUMMARY OF THE INVENTION

The present invention satisfies these purposes by the provision of a relatively rigid, articulated, two-part patient "cover", or enclosure, comprised essentially of two open-bottom shells, hinged to one another, and mounted on and attachable to the longitudinal rails of a conventional hospital bed frame. One part, i.e., the foot part, of the cover has confining side walls on opposite sides of the patient, extending substantially from the foot of the bed to approximately the patient's hips, and has a top joining the upper edges of these side walls from the foot of the bed to a point very approximately half-way back to the hips. The other part, i.e., the head part, encloses the patient's upper body, arms and head. The modern conventional hospital bed has a bed frame which hinges on a horizontal axis at an appropriate point so that the rearward or head and upper body part of the frame, and the portion of the mattress thereon, can be tilted up from horizontal through an angle of say 60°. The rearward or head part of the cover rests on and is clamped to this pivotally mounted head part of the frame so as to swing upwards accordingly.

The front part of a hospital bed frame is often capable of a tilt-up under the knees, and is made of several articulated or jointed frame parts, with suitable bracing. The present embodiment of the invention does not employ this knee tilt-up, and it can be assumed that the forwardly reaching portion of the bed frame is and remains horizontal when equipped with the illustrated embodiment of the present invention. Such knee-tilt may be accommodated in revised forms of the present invention without departure from its generic nature. The present drawings show a more or less conventional means for tilting up the rearward portion of the bed frame and mattress, but this, being old and conventional, will not be described in detail. One figure of the drawing does suggest a conventional arrangement of tilt-up for the knee region, but since this would not be used with the present embodiment of the invention, it will not be described, and it will be assumed the forwardly reaching extent of the bed frame is used without or braced against pivotal actions. If a knee lift is described for patient comfort, it can be accomplished by simply propping up the knees with use of covers.

When the bed frame and mattress are horizontal, and the two pivotally related shells of the cover are correspondingly outstretched into generally horizontal dispositions, the foot part of the shell has a vertical height above the bed frame such as to rise sufficiently above the mattress to afford the patient good, comfortable leg and knee clearance. The head part of the enclosure rises substantially higher, in general proportions as will be seen, for example, from a reference to the accompanying drawings. The two halves overlap somewhat at the sides. To close any otherwise existing gap between the upper rearward edge of the foot part of the shell and the upper forward edge of the head part of the shell, I prefer to use a rearward arcuate extension on the top wall of the foot or front shell, formed on an arc struck about the pivot axis which pivotally relates or connects the foot and head shells, and about which the head portion of bed frame can rock to move the patient toward sitting position. When the pivoted head portion of the bed frame is so tilted up about the pivot axis, this portion, mounted thereon, swings forward about this same axis, and slides telescopically down over the aforementioned arcuate top of the front enclosure.

Various subsidiary features will be noted and will appear in the course of the following detailed description of a present illustrative embodiment of the invention.

BRIEF DESCRIPTION OF THE DRAWINGS

FIG. 1 is a perspective view of the patient cover of the invention, on a hospital bed whose frame is in an up-tilted position to support the patient in a fairly upright, semi-sitting position;

FIG. 2 is a longitudinal vertical section of the bed and cover of FIG. 1, with the bed essentially in side elevation, the bed frame being down in horizontally flat position, the view in this suggesting to an extent conventional equipment for elevation of the head part of the bed frame to sitting position, and with a suggestion of conventional means for elevating or up-tilting the front part of the bed frame in the knee region, as found in modern hospital beds;

FIG. 3 is a section on line 3—3 of FIG. 2; and

FIGS. 4 and 5 are fragmentary detail vertical sections taken transversely through the near sides of the bed frame members, cover walls and mattress support elements, as represented by the lines and arrows 4—4 and 5—5 of FIG. 2.

DETAILED DESCRIPTION OF A PRESENT EMBODIMENT OF THE INVENTION

In the drawings, a conventional or semi-conventional hospital bed is shown generally and somewhat diagrammatically at 10, being comprised essentially of a foot 11, a head 12, and lower longitudinal rails 13.

Rising from a central portion of each of rails 13 is the flat plate stem part 14 of a T-shaped bracket 15, the extremities of whose horizontally and oppositely outstretched arms 16 and 17 provide pivotal supports at 16a and 17a for forwardly and rearwardly reaching mattress-supporting bed frame rails 18 and 19, respectively. The rails 18 and 19 are preferably angle irons, with vertical flanges 20, and inturned horizontal flanges 21 extending from the top edges of the flanges 20, the flanges 21 being formed with gaps at certain locations, such as at 22, for clearance purposes in the regions where the angle irons have pivot joints, as at 17a. In FIG. 1, the bed frame rails 18 and 19 are shown as one piece members, pivotally mounted on T-bracket 15 at 16a and 17a. The pivot at 16a could be omitted for present purposes. In FIG. 2, the bed frame rails 18 are shown more conventionally as comprised of articulated links, pivoted to bracket arm 16 at 16a, in accordance with modern hospital bed design. For the broad purpose of the present description of one illustrative embodiment, the pivot at 16a and the conventional makeup of the rails 18 into articulated links would not have to be used, and if used, the primary reason would be for use of beds already in existence having this feature. Thus, the pivot at 16a and articulation of rails 18 will be ignored as without essential present function. That is to say, broadly, the links 18 will be understood for present purposes to stretch horizontally and to have no effective pivots or articulations.

In the illustrative bed design here shown, the top edge of the T-bracket 15, for the width of the bracket stem 14, has a horizontally inwardly bent flange 24 (FIGS. 2 and 5). The mattress is shown at M, supported by a bedspring S which hooks into the bed frame flanges as appears in FIGS. 4 and 5.

The detailed description to this point is essentially of a suitable example of a hospital bed to which the cover of the invention may be applied.

The patient "cover" C of the invention has two pivotally related relatively rigid "foot" and "head" shells 30 and 31, preferably formed of transparent plastic sheet material, of a thickness of say ⅛ to ¼ inch, and composed typically of Plexiglas sheeting. Air holes such as indicated at 23 will be used in the shells, excepting in certain areas as will appear later.

The foot shell 30 has parallel vertical side walls 33, whose horizontal lower edges 34 may ride on the horizontal flanges 21 and 24 of such a bed frame as described hereinabove. Clamps such as 35 mounted on the outer sides of cover walls 33, near the lower edges of the latter, as at 36 (see FIG. 5), may have upper hinges 37 carrying clamp arms 38 which engage under bed frame arm 16, or angle iron flange 20, as the case may be, and bear screws 38' which when set up clamp the cover walls properly to the bed frame. The shell 30 has also a preferably generally horizontal hood or top wall 40, and a vertical foot-end closure wall 41. The top wall 40 of the shell extends rearwardly from the foot of the bed, to which the shell is clamped by a clamp 44, to a point approximately half-way to a vertical plane containing the pivot 17a, after which it merges into an arcuate wall 45, struck on an arc about pivot 17a as a center, and terminating preferably just beyond the vertical plane defined by the pivot axis 17a at an edge 45a. The side walls 33 rise with the arcuate wall 45 and terminate in substantially vertical edges 33a.

The head or rearward shell 31 has parallel side walls 50, a top wall or hood 51, and a vertical head end wall 52. The side walls 50 of the head end shell 31 preferably project somewhat beyond the edge 33a of the foot shell 30, as to an edge 55 inclined just beyond vertical, so as to provide an extent of overlap or telescopic reception of the left end portion of the shell 33 into the right-hand end portion of the shell 31, as seen in the position of FIG. 2. As can be well seen in FIG. 1 and 2, the top wall 51 of the pivotal rearward shell 31 is notched back to an inset edge 60, located several inches back from the front edge 55 of the side walls 50 of the shell.

The horizontal lower edges 58 of the shell 51 rest on the bed frame flanges 21 to the left of the pivot 17a (as viewed in FIG. 2), and are clamped to the angle irons comprised of the flanges 21 and 20 by clamps 59, like the clamps 35 described above.

The rearward shell 31, thus attached to the bed frame rails 19 pivoted on the horizontal transverse pivot axis at 17a, swings about the axis 17a as the head portion of the bed frame and mattress swing upwardly about said axis, from the horizontal lying down position of FIG. 2, to the sit-up position seen in FIG. 1.

Such tilt-up of the bed frame rails 19 and corresponding portion of the mattress is accomplished by the conventional hand crank mechanism represented generally by the reference numeral 70 in FIG. 2. As the head end portion of the bed, and the shell 31 clamped thereto rise about the axis 17a, the shell 31 rocks down over the arcuate wall 45 of the front shell 30, until the limiting position of FIG. 1 is reached, with the front edges 55 of the side walls rocked down to the position represented in phantom lines, and the inset horizontal top edge 60 in engagement in the angle between the shell top 30 and its arcuate extension 45.

The patient inside the enclosure or cover is not closely confined for reasons of comfort. He can move about, turn side to side, and can be moved from a lying down position, to a sitting up position 60° above horizontal. The top arcuate wall 45 of the front shell and the top 51 of the rearward shell are preferably not only transparent, but devoid of air apertures, to enhance vision therethrough.

Access windows may be provided as desired, for example a window 75 with a hinged cover 76, in the front part, and a window 77, with a hinged cover 78, in the rearward part. Locking devices of any nature may be provided, as suggested at 79. These may be used for passage of food trays, or bed pan. Perfect security is assured by the cover of the invention, which has also various advantages such as simplicity, and resulting low cost of manufacture. Very substantial savings result from the elimination in many cases of otherwise round-the-clock supervision by attendants.

The present embodiment of the invention is to be understood as for the purpose of illustration only, since numerous changes may quite evidently be made in design, structure and arrangement without departing from the spirit and scope of the invention or of the following claims.

What is claimed is:

1. A security enclosure for a patient in a hospital bed of the type having a mattress support frame with head and foot ends and a transverse pivot joint in an intermediate location thereof, dividing said frame into normally horizontally outstretched head and foot portions, said head portion being adjustable between a horizontal lying position and a range of angularly up-tilted sitting positions, comprising:

two relatively rigid patient enclosure shells articulated for pivotal movement relative to one another on a pivot axis substantially coinciding with said transverse pivot joint of said mattress support frame, one of said shells comprising a leg and foot enclosure, and the other of said shells an upper body, arm and head enclosure, with the first adapted for mounting on said foot portion of said support frame, and the second on said head portion thereof, said shells being formed to substantially confine a patient throughout a range of relative positions of said head portion of said bed frame from horizontal to an up-tilted sitting position, said shells having side wall portions adapted to partially and relatively closely overlap one another on each side throughout said pivotal movement of said shells relatively to one another, a top wall for said leg and foot enclosure, formed with a convex rearward extension wall struck on an arc whose center coincides with said pivot axis, and a top wall for the upper body, arm and head enclosure shaped to move with a relatively close fit over said convex rearward extension wall of said leg and foot enclosure when said body, head and arm enclosure swings pivotally upward with said head portion of said bed frame.

* * * * *